(12) United States Patent
Breuer et al.

(10) Patent No.: US 8,338,146 B2
(45) Date of Patent: Dec. 25, 2012

(54) **METHOD FOR PRODUCING OPTICALLY ACTIVE ALCOHOLS USING AN *AZOARCUS* SP. EBN1 DEHYDROGENASE**

(75) Inventors: Michael Breuer, Darmstadt (DE); Ralf Rabus, Bad Zwischenahn (DE); Johann Heider, Marburg (DE)

(73) Assignees: BASF SE, Ludwigshafen (DE); Albert-Ludwigs-Universitaet Freiburg, Freiburg (DE); Max-Planck-Gesellschaft zur Förderung der Wissenschaften e.V., München (DE)

( * ) Notice: Subject to any disclaimer, the term of this patent is extended or adjusted under 35 U.S.C. 154(b) by 293 days.

(21) Appl. No.: 12/665,383

(22) PCT Filed: Jun. 16, 2008

(86) PCT No.: PCT/EP2008/057522
§ 371 (c)(1),
(2), (4) Date: Feb. 12, 2010

(87) PCT Pub. No.: WO2008/155302
PCT Pub. Date: Dec. 24, 2008

(65) Prior Publication Data
US 2010/0143991 A1 Jun. 10, 2010

(30) Foreign Application Priority Data
Jun. 20, 2007 (EP) .................... 07110670

(51) Int. Cl.
*C12P 7/02* (2006.01)
(52) U.S. Cl. .................... 435/155
(58) Field of Classification Search .......... None
See application file for complete search history.

(56) References Cited

U.S. PATENT DOCUMENTS

| 4,310,702 | A | 1/1982 | Masilamani et al. |
| 5,710,341 | A | 1/1998 | Siegel et al. |
| 6,187,956 | B1 | 2/2001 | Klinger et al. |
| 2008/0206824 | A1 | 8/2008 | Sturmer et al. |
| 2009/0325225 | A1 | 12/2009 | Breuer et al. |

FOREIGN PATENT DOCUMENTS

| CN | 101503714 A | 8/2009 |
| EP | 0735016 A1 | 10/1996 |
| WO | WO-00/43345 A1 | 7/2000 |
| WO | WO-2005/108590 A2 | 11/2005 |
| WO | WO-2006/094945 A2 | 9/2006 |
| WO | WO-2007/147897 A1 | 12/2007 |
| WO | WO-2008/055988 A2 | 5/2008 |

OTHER PUBLICATIONS

Uniprot (Jan. 2005) Accession No. Q5P1L5.*
Gardini et al. Tetrahedron 1996, 52, 3547-3552.*
Zheng et al. Appl. Environ. Microbiol. (Jul. 2004) 70 (7), 3807-3713.*
Rabus, R., et al., "The Genome Sequence of an Anaerobic Aromatic-Degrading Denitrifying Bacterium, Strain EbN1", Arch Microbiol, vol. 183, (2005), pp. 27-36.
Guy, A., et al., "Selective α-Chlorination of Alkyl Aryl Ketones", Synthesis, vol. 12, (1982), pp. 1018-1020.
Kajigaeshi, S., et al., "α-Chlorination of Aromatic Acetyl Derivatives with Benzyltrimethylammonium Dichloroiodate", Synthesis, vol. 7, (1988), pp. 545-546.
Sakuraba, S., et al., "Efficient Asymmetric Hydrogenation of ∝-Amino Ketone Derivatives. A Highly Enantioselective Synthesis of Phenylephrine, Levamisole, Carnitine and Propranolol", Chem. Pharm. Bull., vol. 43, No. 5, (1995), pp. 738-747.
Takeda, H., et al., Practical Asymmetric Synthesis of ( R)—(-)-Phenylephrine Hydrochloride Catalyzed by (2R, 4 R̄)-MCCPM-Rhodium Complex), Tetrahedron Letters, vol. 3ō, No. 3̄, (1989), pp. 367-370.
Yang, Y., et al,, "Enzymatic Ketone Reduction: Mapping the Substrate Profile of a Short-Chaine Alcohol Dehydrogenase (YMR226c) from *Saccharomyces cerevisiae*", Tetrahedron: Asymmetry, vol. 18, (2007), pp. 1799-1803.
Groger H., et al. "Preparative asymmetric reduction of ketones in a biphasic medium with an (S)-alcohol dehydrogenase under in situ-cofactor-recycling with a formate dehydrogenase". Tetrahedron, 2004, vol. 60, pp. 633-640.
Hummel Werner, "Large-scale applications of NAD(P)-dependent oxidoreductases: recent developments". Trends Biotecfhnol., 1999, vol. 17, pp. 487-492.

(Continued)

*Primary Examiner* — Nashaat Nashed
(74) *Attorney, Agent, or Firm* — Connolly Bove Lodge & Hutz, LLP

(57) ABSTRACT

A process for preparing optically active alcohols of the formula Ia or Ib

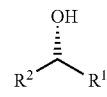

Formula Ia

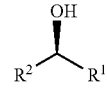

Formula Ib in which
$R^1, R^2$ are alkyl, alkenyl, aryl, or alkylaryl groups which may in turn be substituted one or more times by alkyl, halogen, SH, $SR^2$, OH, $OR^2$, $NO_2$, CN, CO, $COOR^2$, $NR^2R^3$ or $NR^2R^3R^{4+}X$, where $R^2$, $R^3$ and $R^4$ are independently of one another H or a lower alkyl or lower alkoxy radical, and $X^-$ is a counter ion, with the proviso that $R^1$ is not equal to $R^2$,
by reducing the corresponding ketone, where the reduction is carried out with a dehydrogenase having the polypeptide sequence of SEQ ID NO: 2 or NO: 4, or with a polypeptide sequence in which up to 25% of the amino acid residues are altered by comparison with SEQ ID NO: 2 or NO: 4 by deletion, insertion, substitution or a combination thereof.

7 Claims, 1 Drawing Sheet

OTHER PUBLICATIONS

Bradshaw C. W., et al. "Lactobacillus kefir Alcohol Dehydrogenase: A Useful Catalyst for Synthesis". J. Org. Chem. 1992, vol. 57, pp. 1532-1536.

Database EMBL—UniProtKB Q5P1L5_AZOSE; "Short-chain dehydrogenase/reductase, possibly involved in polyhydroxybutyrate (PHB) synthesis." May 29, 2007.

* cited by examiner

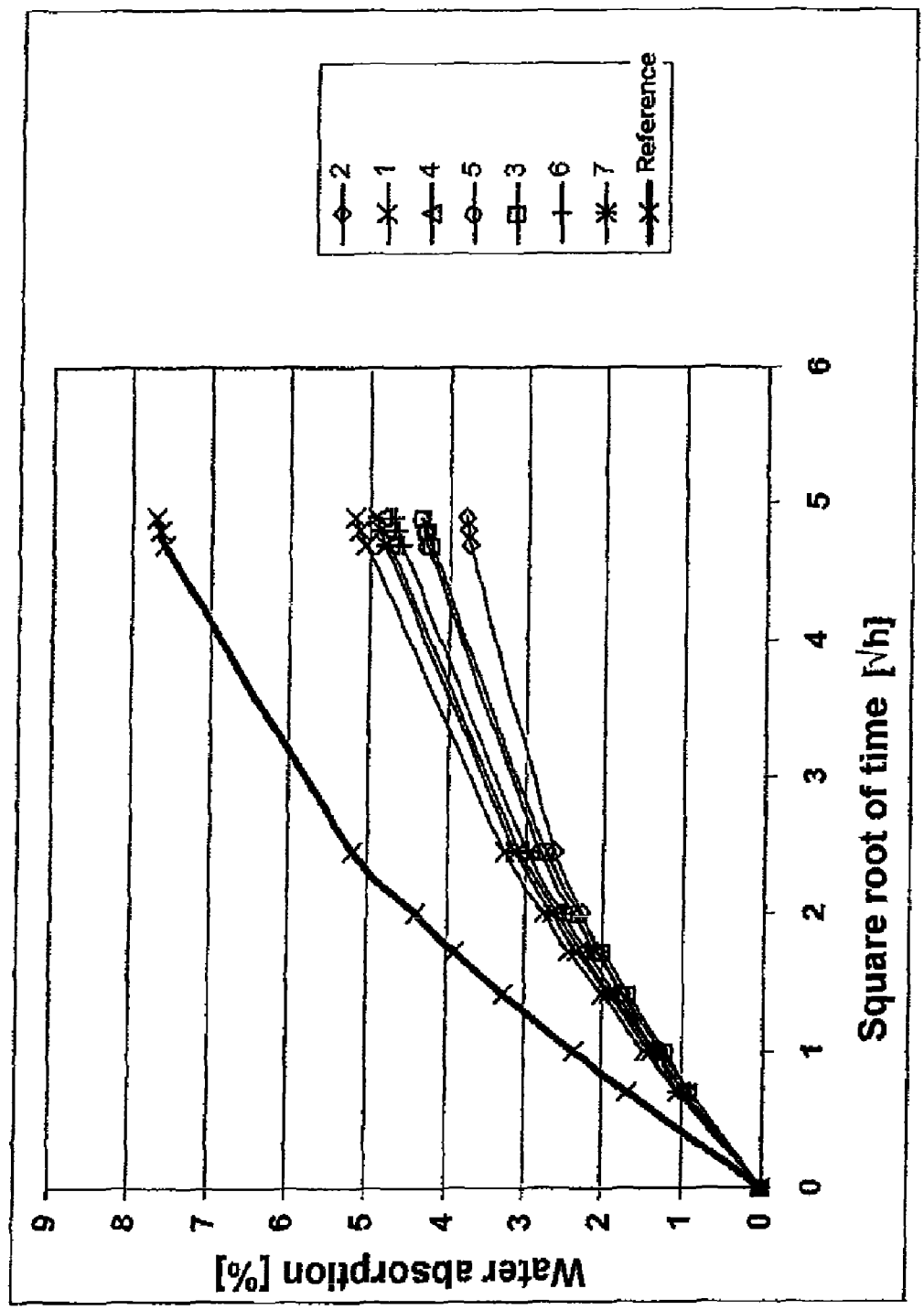

METHOD FOR PRODUCING OPTICALLY ACTIVE ALCOHOLS USING AN *AZOARCUS* SP. EBN1 DEHYDROGENASE

RELATED APPLICATIONS

This application is a national stage application under 35 U.S.C. §371 of PCT/EP2008/057522, filed Jun. 16, 2008, which claims benefit of European application 07110670.2, filed Jun. 20, 2007.

SUBMISSION OF SEQUENCE LISTING

The Sequence Listing associated with this application is filed in electronic format via EFS-Web and hereby is incorporated by reference into the specification in its entirety. The name of the text file containing the Sequence Listing is Sequence_Listing_12810_00970_ST25.txt. The size of the text file is 12.5 kb; the text file was created on Dec. 17, 2009.

The present invention relates to a process for preparing optically active alcohols of the formula Ia or Ib

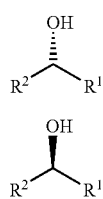

Formula Ia

Formula Ib

PRIOR ART

The function of dehydrogenases as biocatalysts is generally known [*Chemico-Biological Interactions* (2003) 143: 247, *Journal of Biological Chemistry* (2002) 277:25677]. In particular, the industrial use of this enzyme class for preparing fine chemicals is documented [*Tetrahedron* (2004) 60:633, *Trends Biotechnol* (1999) 17:487]. The known dehydrogenases differ in their activity and specificity depending on the substrate. They are differentiated according to their stereoselectivity into so-called 'Prelog' and 'anti'-Prelog enzymes (*Pure and Applied Chemistry*, (1964), 9:119).

Thus, the biocatalysts described for preparing optically active phenylethanol derivatives are chiefly those exhibiting 'Prelog' selectivity, enzymes exhibiting the contrary enantioselectivity are rarer, although not unknown [*Trends Biotechnol* (1999) 17:487, *J. Org. Chem.* (1992) 57:1532].

The present invention relates to a process for preparing optically active alcohols of the formula Ia or Ib

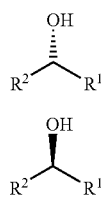

Formula Ia

Formula Ib in which
$R^1$, $R^2$ are alkyl, alkenyl, aryl, or alkylaryl groups which may in turn be substituted one or more times by alkyl, halogen, SH, $SR^2$, OH, $OR^2$, $NO_2$, CN, CO, $COOR^2$, $NR^2R^3$ or $NR^2R^3R^{4+}X$, where $R^2$, $R^3$ and $R^4$ are independently of one another H or a lower alkyl or lower alkoxy radical, and $X^-$ is a counter ion, with the proviso that $R^1$ is not equal to $R^2$, by reducing the corresponding ketone, where the reduction is carried out with a dehydrogenase having the polypeptide sequence of SEQ ID NO: 2 or SEQ ID NO: 4, or with a polypeptide sequence in which up to 25% of the amino acid residues are altered by comparison with SEQ ID NO: 2 or SEQ ID NO: 4 by deletion, insertion, substitution or a combination thereof.

A particularly good embodiment of the invention consists of a process for preparing optically active alcohols of the formula Ia or Ib in which $R^1$ is C1-C10-alkyl and $R^2$ is phenyl, where the radicals R1 and/or R2 are optionally monosubstituted by halogen.

The present invention relates in particular to a process for preparing optically active alcohols of the formula Ia, where the radical $R^1$ is less bulky than $R^2$.

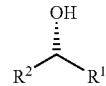

Formula Ia

If the $R^2$ radical is more bulky than the $R^1$ radical, the alcohol is allocated, in accordance with Prelog, V., *Pure and Applied Chemistry*, (1964), 9, 119-130, to the 'anti'-Prelog category.

Chiral alcohols can be differentiated on the basis of their configuration into so-called 'Prelog' and 'anti-Prelog' enantiomers. The assignment to one of the two categories takes place according to the size (bulk) of the two groups which are adjacent to the alcohol group, and the alignment of the hydroxy function in relation to these two groups. Optically active alcohols with 'anti-Prelog' configuration are important precursors for various active ingredients.

General Terms and Definitions

Unless indicated otherwise, the following general meanings apply:

"Halogen" stands for fluorine, chlorine, bromine, or iodine, in particular fluorine or chlorine.

"Lower alkyl" stands for straight-chain or branched alkyl radicals having 1 to 6 C atoms, such as methyl, ethyl, i- or n-propyl, n-, i-, sec- or tert-butyl, n-pentyl or 2-methylbutyl, n-hexyl, 2-methylpentyl, 3-methylpentyl, 2-ethylbutyl.

"Lower alkenyl" stands for the mono- or polyunsaturated, preferably mono- or diunsaturated, analogs of the abovementioned alkyl radicals having 2 to 6 carbon atoms, where the double bond may be present in any position of the carbon chain.

"Lower alkoxy" stands for the oxygen-terminated analogs of the above alkyl radicals.

"Aryl" stands for a mono- or polynuclear, preferably mono- or dinuclear, optionally substituted aromatic radical, in particular for phenyl or for a naphthyl bonded via any ring position, such as 1- or 2-naphthyl. These aryl radicals may optionally have 1 or 2 identical or different substituents, for example halogen, lower alkyl, lower alkoxy as defined above, or trifluoromethyl.

"Enantioselectivity" in the context of the present invention means that the enantiomeric excess ee (in %) of one of the two possible enantiomers is at least 50%, preferably at least 80%, in particular at least 90% and specifically at least 95%. The ee is calculated as follows:

$$ee(\%) = \text{enantiomer } A - \text{enantiomer } B/(\text{enantiomer } A + \text{enantiomer } B) \times 100$$

Biochemical Embodiments

Particularly suitable dehydrogenases (EC 1.1.X.X) are especially NAD- or NADP-dependent dehydrogenases (E.C. 1.1.1.x), in particular alcohol dehydrogenases (E.C.1.1.1.1 or E.C.1.1.1.2) which bring about selective reduction of the ketone to the 'anti-Prelog' alcohol. The dehydrogenase is preferably obtained from a microorganism, particularly preferably from a bacterium, a fungus, in particular a yeast, in each case deposited in collections of strains or obtainable from isolates of natural sources, such as soil samples, biomass samples and the like or by de novo-gene synthesis.

The dehydrogenase can be used in purified or partially purified form or in the form of the original microorganism or of a recombinant host organism which expresses the dehydrogenase. Processes for obtaining and purifying dehydrogenases from microorganisms are sufficiently well known to the skilled worker, e.g. from K. Nakamura & T. Matsuda, "Reduction of Ketones" in K. Drauz and H. Waldmann, Enzyme Catalysis in Organic Synthesis 2002, Vol. III, 991-1032, Wiley-VCH, Weinheim. Recombinant processes for generating dehydrogenases are likewise known, for example from W. Hummel, K. Abokitse, K. Drauz, C. Rollmann and H. Gröger, Adv. Synth. Catal. 2003, 345, No. 1+2, pp. 153-159.

Suitable bacteria are for example those of the orders of Burkholderiales, Hydrogenophilales, Methylophilales, Neisseriales, Nitrosomonadales, Procabacteriales or Rhodocyclales.

Particularly preferred dehydrogenases are those from the family of Rhodocyclaceae.

Particularly preferred dehydrogenases are from the genera *Azoarcus Azonexus, Azospira, Azovibrio, Dechloromonas, Ferribacterium, Petrobacter, Propionivibrio, Quadricoccus, Rhodocyclus, Sterolibacterium, Thauera* and *Zoogloea*.

Especially preferred dehydrogenases are from species of the genus *Azoarcus*.

The reduction with the dehydrogenase normally takes place in the presence of a suitable cofactor (also referred to as cosubstrate). The cofactor normally used for reducing the ketone is NADH and/or NADPH. It is possible besides to employ dehydrogenases as cellular systems which intrinsically comprise cofactor, or alternative redox mediators can be added (A. Schmidt, F. Hollmann and B. Bühler "Oxidation of Alcohols" in K. Drauz and H. Waldmann, Enzyme Catalysis in Organic Synthesis 2002, Vol. III, 991-1032, Wiley-VCH, Weinheim).

The reduction with the dehydrogenase normally additionally takes place in the presence of a suitable reducing agent which regenerates the cofactor oxidized during the reduction.

Examples of suitable reducing agents are sugars, especially the hexoses such as glucose, mannose, fructose, and/or oxidizable alcohols, especially ethanol, propanol, butanol, pentanol or isopropanol, and formate, phosphite or molecular hydrogen. To oxidize the reducing agent and, connected therewith, to regenerate the coenzyme it is possible to add a second dehydrogenase such as, for example, glucose dehydrogenase when glucose is used as reducing agent, phosphite dehydrogenase when phosphite is used as reducing agent or formate dehydrogenase when formate is used as reducing agent. This dehydrogenase can be employed as free or immobilized enzyme or in the form of free or immobilized cells. Preparation thereof is possible either separately or by coexpression in a (recombinant) dehydrogenase strain.

The dehydrogenases used according to the invention can be employed free or immobilized. An immobilized enzyme means an enzyme which is fixed to an inert carrier. Suitable carrier materials, and the enzymes immobilized thereon, are disclosed in EP-A-1149849, EP-A-1069183 and DE-A 100193773, and the references cited therein. The disclosure of these publications in this regard is incorporated in its entirety herein by reference. Suitable carrier materials include for example clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The carrier materials are normally employed in a finely divided particulate form to prepare the carrier-bound enzymes, with preference for porous forms. The particle size of the carrier material is normally not more than 5 mm, in particular not more than 2 mm (grading curve). It is possible analogously to choose a free or immobilized form on use of the dehydrogenase as whole-cell catalyst. Examples of carrier materials are Ca alginate and carrageenan. Both enzymes and cells can also be crosslinked directly with glutaraldehyde (crosslinking to give CLEAs). Corresponding and further immobilization methods are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim.

The reaction can be carried out in aqueous or nonaqueous reaction media or in 2-phase systems or (micro)emulsions. The aqueous reaction media are preferably buffered solutions which ordinarily have a pH of from 4 to 8, preferably from 5 to 8. The aqueous solvent may, besides water, additionally comprise at least one alcohol, e.g. ethanol or isopropanol, or dimethyl sulfoxide.

Nonaqueous reaction media mean reaction media which comprise less than 1% by weight, preferably less than 0.5% by weight, of water based on the total weight of the reaction medium. The reaction is preferably carried out in an organic solvent. Examples of suitable solvents are aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, tetrachloromethane, dichloroethane or tetrachloroethane, aromatic hydrocarbons, such as benzene, toluene, the xylenes, chlorobenzene or dichlorobenzene, aliphatic acyclic and cyclic ethers or alcohols, preferably having 4 to 8 carbon atoms, such as diethyl ether, methyl tent-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof.

The reduction with the dehydrogenase is carried out for example in an aqueous-organic, in particular aqueous, reaction medium.

The ketone to be reduced is preferably employed in a concentration of from 0.1 g/l to 500 µl, particularly preferably from 1 g/l to 50 g/l, in the enzymatic reduction and can be fed in continuously or discontinuously.

The enzymatic reduction ordinarily takes place at a reaction temperature below the deactivation temperature of the dehydrogenase employed and preferably at −10° C. at least. It is particularly preferably in the range from 0 to 100° C., in particular from 15 to 60° C. and specifically from 20 to 40° C., e.g. at about 30° C.

A possible procedure is for example to mix the ketone with the dehydrogenase, the solvent and, if desired, the coenzymes, if desired a second dehydrogenase to regenerate the coenzyme and/or further reducing agents, thoroughly, e.g. by stirring or shaking. However, it is also possible to immobilize the dehydrogenase(s) in a reactor, for example in a column, and to pass a mixture comprising the ketone and, if desired, coenzymes and/or cosubstrates through the reactor. For this purpose, the mixture can be circulated through the reactor until the desired conversion is reached. In this case, the keto group of the ketone is reduced to an OH group, resulting in substantially one of the two enantiomers of the alcohol. The reduction is ordinarily managed until the conversion is at least 70%, particularly preferably at least 85% and especially at least 95%, based on the ketone present in the mixture. The progress of the reaction, i.e. the sequential reduction of the ketone, can in this case be followed by conventional methods such as gas chromatography or high-pressure liquid chromatography.

The dehydrogenases employed in the process of the invention are particularly preferably alcohol dehydrogenases having the following properties:

Alcohol dehydrogenase from *Azoarcus* having an amino acid sequence shown in SEQ ID NO: 2 or SEQ ID NO: 4, and alcohol dehydrogenases having amino acid sequences in which up to 25%, preferably up to 15%, particularly preferably up to 10, especially up to 5%, of the amino acid residues are altered by comparison with SEQ ID NO: 2 or SEQ ID NO: 4 by deletion, insertion, substitution or a combination thereof.

Oxidation of simple alcohols such as, for example, isopropanol, butan-2-ol, pentan-2-ol or cyclohexanol to the corresponding carbonyl with simultaneous reduction of $NAD^+$ or $NADP^+$.

Alcohol dehydrogenases which catalyze the reduction in an enantiomeric purity of at least 95% ee (in the presence of NADH and/or NADPH; at 30° C. and pH 7.0).

The present invention further relates also to an 'anti-Prelog' dehydrogenase having at least one of the aforementioned properties.

The alcohol dehydrogenases exhibit activity in the presence of the following solvents: heptane, hexane, MtBE, n-butanol, butan-2-ol, n-pentanol, pentan-2-ol, pentan-3-ol, DMSO 1-propanol, n-propanol, ethanol.

They preferably have a molecular weight in the region of 26±2 kdaltons.

Further modifications of dehydrogenases of the invention: the invention likewise comprises "functional equivalents" of the specifically disclosed enzymes having dehydrogenase activity and the use thereof in the processes of the invention.

"Functional equivalents" or analogs of the specifically disclosed enzymes are in the context of the present invention polypeptides which differ therefrom and which still have the desired biological activity such as, for example, substrate specificity. Thus, "functional equivalents" mean for example enzymes which reduce from the ketone to the corresponding 'anti-Prelog' alcohol and which have at least 20%, preferably 50%, particularly preferably 75%, very particularly preferably 90% of the activity of an enzyme comprising one of the amino acid sequences listed under SEQ ID NO: 2 or SEQ ID NO: 4. Functional equivalents are additionally preferably stable between pH 4 to 10 and advantageously have a pH optimum between pH 5 and 8 and a temperature optimum in the range from 20° C. to 80° C.

"Functional equivalents" also mean according to the invention in particular mutants which have an amino acid other than that specifically mentioned in at least one sequence position of the abovementioned amino acid sequences but nevertheless have one of the abovementioned biological activities. "Functional equivalents" thus comprise the mutants obtainable by one or more amino acid additions, substitutions, deletions and/or inversions, it being possible for said modifications to occur in any sequence position as long as they lead to a mutant having the property profile according to the invention. Functional equivalence also exists in particular when the reactivity patterns agree qualitatively between mutant and unmodified polypeptide, i.e. for example identical substrates are converted at a different rate.

Examples of suitable amino acid substitutions are to be found in the following table:

| Original residue | Examples of the substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the described polypeptides, and "functional derivatives" and "salts" of the polypeptides.

"Precursors" are in this connection natural or synthetic precursors of the polypeptides with or without the desired biological activity.

The term "salts" means both salts of carboxyl groups and acid addition salts of amino groups of the protein molecules of the invention. Salts of carboxyl groups can be prepared in a manner known per se and comprise inorganic salts such as, for example, sodium, calcium, ammonium, iron and zinc salts, and salts with organic bases such as, for example, amines, such as triethanolamine, arginine, lysine, piperidine and the like. The invention also relates to acid addition salts such as, for example, salts with mineral acids such as hydrochloric acid or sulfuric acid, and salts with organic acids such as acetic acid and oxalic acid.

"Functional derivatives" of polypeptides of the invention can likewise be prepared on functional amino acid side groups or on their N- or C-terminal end with the aid of known techniques. Such derivatives comprise for example aliphatic esters of carboxylic acid groups, amides of carboxylic acid groups, obtainable by reaction with ammonia or with a primary or secondary amine; N-acyl derivatives of free amino groups prepared by reaction with acyl groups; or O-acyl derivatives of free hydroxy groups prepared by reaction with acyl groups.

In the case where protein glycosylation is possible, "functional equivalents" of the invention comprise proteins of the type designated above in deglycosylated or glycosylated form, and modified forms obtainable by altering the glycosylation pattern.

"Functional equivalents" of course also comprise polypeptides which are obtainable from other organisms, and naturally occurring variants. For example, it is possible to establish ranges of homologous sequence regions by comparison of sequences, and to ascertain equivalent enzymes based on the specific requirements of the invention.

"Functional equivalents" likewise comprise fragments, preferably individual domains or sequence motifs, of the polypeptides of the invention, which have, for example, the desired biological function.

"Functional equivalents" are additionally fusion proteins which comprise one of the abovementioned polypeptide sequences or functional equivalents derived therefrom and at least one further, heterologous sequence which is functionally different therefrom and is in functional N- or C-terminal linkage (i.e. with negligible mutual functional impairment of the parts of the fusion protein). Nonlimiting examples of such heterologous sequences are, for example, signal peptides or enzymes.

"Functional equivalents" also comprised in the invention are homologues of the specifically disclosed proteins. These have at least 75%, in particular at least 85%, such as, for example, 90%, 95%, 97% or 99%, homology to one of the specifically disclosed amino acid sequences, calculated by the algorithm of Pearson and Lipman, Proc. Natl. Acad, Sci. (USA) 85(8), 1988, 2444-2448. A percentage homology of a homologous polypeptide of the invention means in particular percentage identity of the amino acid residues based on the total length of one of the amino acid sequences specifically described herein.

Homologues of the proteins or polypeptides of the invention can be generated by mutagenesis, e.g. by point mutation or truncation of the protein.

Homologues of the proteins of the invention can be identified by screening combinatorial libraries of mutants, such as, for example, truncation mutants. For example, a variegated library of protein variants can be generated by combinatorial mutagenesis at the nucleic acid level, such as, for example, by enzymatic ligation of a mixture of synthetic oligonucleotides. There is a large number of methods which can be used to prepare libraries of potential homologues from a degenerate oligonucleotide sequence. Chemical synthesis of a degenerate gene sequence can be carried out in an automatic DNA synthesizer, and the synthetic gene can then be ligated into a suitable expression vector. Use of a degenerate set of genes makes it possible to provide all the sequences which encode the desired set of potential protein sequences in one mixture. Methods for synthesizing degenerate oligonucleotides are known to the skilled worker (e.g. Narang, S. A. (1983) Tetrahedron 39:3; Itakura et al. (1984) Annu. Rev. Biochem, 53:323; Itakura et al., (1984) Science 198:1056; Ike et al. (1983) Nucleic Acids Res. 11:477).

Several techniques are known in the art for screening gene products of combinatorial libraries which have been prepared by point mutations or truncation, and for screening cDNA libraries for gene products having a selected property. These techniques can be adapted to the rapid screening of gene libraries which have been generated by combinatorial mutagenesis of homologues of the invention. The most commonly used techniques for screening large gene libraries, which are subject to high-throughput analysis, comprise the cloning of the gene library into replicable expression vectors, transformation of suitable cells with the resulting vector library and expression of the combinatorial genes under conditions under which detection of the desired activity facilitates isolation of the vector which encodes the gene whose product has been detected. Recursive ensemble mutagenesis (REM), a technique which increases the frequency of functional mutants in the libraries, can be used in combination with the screening tests to identify homologues (Arkin and Yourvan (1992) PNAS 89:7811-7815; Delgrave et al. (1993) Protein Engineering 6(3):327-331).

Further Configuration of Coding Nucleic Acid Sequences of the Invention

The invention relates to the use of nucleic acid sequences (single- and double-stranded DNA and RNA sequences, such as, for example, cDNA and mRNA) which code for an enzyme having dehydrogenase activity according to the invention. Preferred nucleic acid sequences code for example for amino acid sequences shown in SEQ ID NO: 2 or SEQ ID NO: 4 or characteristic partial sequences thereof, or comprise nucleic acid sequences shown in SEQ ID NO: 1 or SEQ ID NO: 3 or characteristic partial sequences thereof.

All nucleic acid sequences mentioned herein can be prepared in a manner known per se by chemical synthesis from the nucleotide building blocks, such as, for example, by fragment condensation of individual overlapping complementary nucleic acid building blocks of the double helix. Chemical synthesis of oligonucleotides can take place for example in a known manner by the phosphoamidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods are described in Sambrook et al. (1989), Molecular Cloning: A laboratory manual, Cold Spring Harbor Laboratory Press.

The invention also relates to nucleic acid sequences (single- and double-stranded DNA and RNA sequences, such as, for example, cDNA and mRNA), coding for one of the above polypeptides and their functional equivalents which are obtainable for example by using artificial nucleotide analogs.

The invention relates both to isolated nucleic acid molecules which code for polypeptides or proteins of the invention or biologically active sections thereof, and to nucleic acid fragments which can be used for example for use as hybridization probes or primers for identifying or amplifying coding nucleic acids of the invention.

The nucleic acid molecules of the invention may additionally comprise untranslated sequences from the 3' and/or 5' end of the coding gene region.

The invention further comprises the nucleic acid molecules which are complementary to the specifically described nucleotide sequences, or a section thereof.

The nucleotide sequences of the invention make it possible to generate probes and primers which can be used to identify and/or clone homologous sequences in other cell types and organisms. Such probes or primers usually comprise a nucleotide sequence region which hybridizes under "stringent" conditions (see below) to at least about 12, preferably at least about 25, such as, for example, about 40, 50 or 75, consecutive nucleotides of a sense strand of a nucleic acid sequence of the invention or a corresponding antisense strand.

An "isolated" nucleic acid molecule is separated from other nucleic acid molecules which are present in the natural source of the nucleic acid, and may moreover be substantially free of other cellular material or culture medium if it is prepared by recombinant techniques, or free of chemical precursors or other chemicals if it is synthesized chemically.

A nucleic acid molecule of the invention can be isolated by standard techniques of molecular biology and with the aid of the sequence information provided according to the invention. For example, cDNA can be isolated from a suitable cDNA library by using one of the specifically disclosed complete sequences or a segment thereof as hybridization probe and standard hybridization techniques (as described for example in Sambrook, J., Fritsch, E. F. and Maniatis, T. Molecular Cloning: A Laboratory Manual. $2^{nd}$ edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof can be isolated by polymerase chain reaction, using the oligonucleotide primers constructed on the basis of this sequence. The nucleic acid amplified in this way can be cloned into a suitable vector and be characterized by DNA sequence analysis. The oligonucleotides of the invention can also be prepared by standard synthetic methods, e.g. using an automatic DNA synthesizer.

The nucleic acid sequences of the invention can in principle be identified and isolated from all organisms. The nucleic acid sequences of the invention or the homologues thereof can advantageously be isolated from fungi, yeasts, archaea or bacteria. Bacteria which may be mentioned are gram-negative and gram-positive bacteria. The nucleic acids of the invention are preferably from gram-negative bacteria, advantageously from α-proteobacteria, β-proteobacteria or γ-proteobacteria, particularly preferably from bacteria of the orders of Burkholderiales, Hydrogenophilales, Methylophilales, Neisseriales, Nitrosomonadales, Procabacteriales or Rhodocyclales. Very particularly preferably from bacteria of the family of Rhodocyclaceae, Particularly preferably from the genus *Azoarcus*. Particularly preferably from species *Azoarcus anaerobius, Azoarcus buckelii, Azoarcus communis, Azoarcus evansii, Azoarcus indigens, Azoarcus toluclasticus, Azoarcus tolulyticus, Azoarcus toluvorans, Azoarcus* sp., *Azoarcus* sp. 22Lin, *Azoarcus* sp. BH72, *Azoarcus* sp. CC-11, *Azoarcus* sp. CIB, *Azoarcus* sp. CR23, *Azoarcus* sp. EB1, *Azoarcus* sp. EbN1, *Azoarcus* sp. FL05, *Azoarcus* sp. HA, *Azoarcus* sp. HxN1, *Azoarcus* sp. mXyN1, *Azoarcus* sp. PbN1, *Azoarcus* sp. PH002, *Azoarcus* sp. T and *Azoarcus* sp. ToN1.

Dehydrogenases from *Azoarcus* sp EbN1 are particularly preferably used.

Nucleic acid sequences of the invention can be isolated for example by conventional hybridization processes or the PCR technique from other organisms, e.g. through genomic or cDNA libraries. These DNA sequences hybridize under standard conditions with the sequences of the invention. It is advantageous to use for the hybridization short oligonucleotides of the conserved regions, for example from the active center, which can be ascertained by comparisons with a dehydrogenase of the invention in a manner known to the skilled worker. However, longer fragments of the nucleic acids of the invention, or the complete sequences, can also be used for the hybridization. These standard conditions vary depending on the nucleic acid used (oligonucleotide, longer fragment or complete sequence) or depending on which type of nucleic acid, DNA or RNA, are used for the hybridization. Thus, for example, the melting temperatures for DNA:DNA hybrids are about 10° C. lower than those of DNA:RNA hybrids of the same length.

Standard conditions mean for example, depending on the nucleic acid, temperatures between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide such as, for example, 42° C. in 5×SSC, 50% formamide. The hybridization conditions for DNA:DNA hybrids are advantageously 0.1×SSC with temperatures between about 20° C. to 45° C., preferably between about 30° C. to 45° C. The hybridization conditions for DNA:RNA hybrids are advantageously 0.1×SSC with temperatures between about 30° C. to 55° C., preferably between about 45° C. to 55° C. These stated temperatures for the hybridization are calculated values for the melting temperature by way of example for a nucleic acid with a length of about 100 nucleotides and a G+C content of 50% in the absence of formamide. The experimental conditions for DNA hybridization are described in relevant text books of genetics, such as, for example, Sambrook et al., "Molecular Cloning", Cold Spring Harbor Laboratory, 1989, and can be calculated by formulae known to the skilled worker, for example depending on the length of the nucleic acids, the type of hybrids or the G+C content. Further information on hybridization can be found by the skilled worker in the following text books: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the specifically disclosed or derivable nucleic acid sequences.

Thus, further nucleic acid sequences of the invention can be derived from SEQ ID NO: 1 or SEQ ID NO: 3 and differ therefrom by addition, substitution, insertion or deletion of single or multiple nucleotides, but still code for polypeptides having the desired property profile.

The invention also comprises nucleic acid sequences which comprise so-called silent mutations or are modified according to the codon usage of a specific original or host organism by comparison with a specifically mentioned sequence, as well as naturally occurring variants such as, for example, splice variants or allelic variants thereof.

It likewise relates to sequences obtainable by conservative nucleotide substitutions (i.e. the relevant amino acid is replaced by an amino acid of the same charge, size, polarity and/or solubility).

The invention also relates to the molecules derived from the specifically disclosed nucleic acids through sequence polymorphisms. These genetic polymorphisms may exist between individuals within a population owing to natural variation. These natural variations normally result in a variance of from 1 to 5% in the nucleotide sequence of a gene.

Derivatives of a nucleic acid sequence of the invention mean for example allelic variants which exhibit at least 40% homology at the derived amino acid level, preferably at least 60% homology, very particularly preferably at least 80, 85, 90, 93, 95 or 98% homology over the entire sequence region (concerning homology at the amino acid level, reference may be made to the above statements about the polypeptides). The homologies may advantageously be higher over partial regions of the sequences.

Derivatives also mean in addition homologues of the nucleic acid sequences of the invention, for example fungal or bacterial homologues, truncated sequences, single-stranded DNA or RNA of the coding and noncoding DNA sequence. They possess for example at the DNA level a homology of at least 40%, preferably of at least 60%, particularly preferably of at least 70%, very particularly preferably of at least 80% over the entire DNA region indicated.

Derivatives additionally mean for example fusions with promoters. The promoters which are upstream of the indicated nucleotide sequences may be modified by one or more nucleotide exchanges, insertions, inversions and/or deletions but without impairing the functionality or activity of the promoters. The promoters may in addition have their activity increased through modification of their sequence, or be completely replaced by more efficient promoters even of organisms of different species.

Derivatives also mean variants whose nucleotide sequence in the region from −1 to −1000 bases upstream of the start codon or 0 to 1000 bases downstream of the stop codon have been modified in such a way that gene expression and/or protein expression is altered, preferably increased.

The invention further comprises also nucleic acid sequences which hybridize with the abovementioned coding sequences under "stringent conditions". These polynucleotides can be found by screening genomic or cDNA libraries and if appropriate be amplified therefrom using suitable primers by means of PCR and then isolated for example using suitable probes. It is additionally possible to synthesize polynucleotides of the invention also by a chemical route. By this property is meant the ability of a poly- or oligonucleotide to bind under stringent conditions to a virtually complementary sequence, whereas nonspecific bindings between noncomplementary partners do not occur under these conditions. For this purpose, the sequences should be 70-100%, preferably 90-100%, complementary. The property of complementary sequences being able to bind specifically to one another is made use of, for example, in the Northern or Southern blotting technique or in the case of primer binding in PCR or RT-PCR. Oligonucleotides with a length of 30 base pairs or more are normally employed for this purpose. Stringent conditions mean for example in the Northern blotting technique the use of a washing solution at 50-70° C., preferably 60-65° C., for example 0.1×SSC buffer with 0.1% SDS (20×SSC: 3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and is described, for example, in Ausubel et al., Current Protocols in Molecular Biology, John Wiley & Sons, N.Y. (1989), 6.3.1-6.3.6.

Configurations of Constructs of the Invention

The invention additionally relates to expression constructs comprising a nucleic acid sequence which codes for a polypeptide of the invention and is under the genetic control of regulatory nucleic acid sequences; and to vectors comprising at least one of these expression constructs.

Such constructs of the invention preferably comprise a promoter 5'-upstream from the respective coding sequence and a terminator sequence 3'-downstream and, if desired, further conventional regulatory elements, in particular in each case operatively linked to the coding sequence.

An "operative linkage" means the sequential arrangement of promoter, coding sequence, terminator and, if desired, further regulatory elements in such a way that each of the regulatory elements is able to perform its function as intended in the expression of the coding sequence. Examples of sequences which can be operatively linked are targeting sequences, and enhancers, polyadenylation signals and the like. Further regulatory elements comprise selectable markers, amplification signals, origins of replication and the like. Suitable regulatory sequences are described for example in Goeddel, Gene Expression Technology: Methods in Enzymology 185, Academic Press, San Diego, Calif. (1990).

A nucleic acid construct of the invention means in particular those in which the gene for a dehydrogenase of the invention has been operatively or functionally linked to one or more regulatory signals to control, e.g. increase, gene expression.

In addition to these regulatory sequences it is possible for the natural regulation of these sequences still to be present in front of the actual structural genes and, if desired, to have been genetically modified so that the natural regulation has been switched off and the expression of the genes has been increased. The nucleic acid construct may, however, also have a simpler structure, i.e. no additional regulatory signals have been inserted in front of the coding sequence, and the natural promoter with its regulation has not been deleted. Instead, the natural regulatory sequence is mutated in such a way that regulation no longer takes place and gene expression is increased.

A preferred nucleic acid construct advantageously also comprises one or more of the previously mentioned "enhancer" sequences functionally linked to the promoter, which make increased expression of the nucleic acid sequence possible. Additional advantageous sequences may also be inserted at the 3' end of the DNA sequences, such as further regulatory elements or terminators. The nucleic acids of the invention may be present in one or more copies in the construct. The construct may also comprise further markers such as antibiotic resistances or auxotrophy-complementing genes, if desired for selecting for the construct.

Advantageous regulatory sequences for the process of the invention are for example present in promoters such as cos, tac, trp, tet, trp-tet, lpp, lac, lpp-lac, lacI$^q$, T7, T5, T3, gal, trc, ara, rhaP (rhaP$_{BAD}$) SP6, lambda-P$_R$ or in the lambda-P$_L$ promoter, which are advantageously used in gram-negative bacteria. Further advantageous regulatory sequences are present for example in the gram-positive promoters amy and SPO2, in the yeast or fungal promoters ADC1, MFalpha, AC, P-60, CYC1, GAPDH, TEF, rp28, ADH. Also advantageous in this connection are the promoters of pyruvate decarboxylase and methanol oxidase, for example from *Hansenula*. It is also possible to use artificial promoters for the regulation.

For expression in a host organism, the nucleic acid construct is advantageously inserted into a vector such as, for example, a plasmid or a phage which makes optimal expression of the genes in the host possible. Vectors mean apart from plasmids and phages also all other vectors known to the skilled worker, e.g. viruses such as SV40, CMV, baculovirus and adenovirus, transposons, IS elements, phasmids, cosmids, and linear or circular DNA. These vectors may undergo autonomous replication in the host organism, or chromosomal replication. These vectors represent a further configuration of the invention. Suitable plasmids are for example in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, lgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. Said plasmids represent a small selection of the possible plasmids. Further plasmids are well known to the skilled worker and can be found for example in the book Cloning Vectors (Eds. Pouwels P. H. et al. Elsevier, Amsterdam-New York-Oxford, 1985, ISBN 0 444 904018).

The nucleic acid construct advantageously comprises, for expression of the further genes present, additionally 3'- and/or 5'-terminal regulatory sequences to increase the expression, which are selected for optimal expression depending on the gene or genes and on the host organism selected.

These regulatory sequences are intended to make specific expression of the genes and of protein expression possible. This may mean, for example depending on the host organism, that the gene is expressed or overexpressed only after induction, or that it is immediately expressed and/or overexpressed.

The regulatory sequences or factors may moreover preferably influence positively, and thus increase, expression of the introduced genes. Thus, enhancement of the regulatory elements can take place advantageously at the level of transcription, by using strong transcription signals such as promoters and/or "enhancers". However, it is also possible in addition to enhance translation by, for example, improving the stability of the mRNA.

In a further embodiment of the vector, the vector comprising the nucleic acid construct of the invention or the nucleic acid of the invention may also advantageously be introduced in the form of a linear DNA into the microorganisms and be integrated by heterologous or homologous recombination into the genome of the host organism. This linear DNA may consist of a linearized vector such as a plasmid or only of the nucleic acid construct or of the nucleic acid of the invention.

For optimal expression of heterologous genes in organisms, it is advantageous to modify the nucleic acid sequences to accord with the specific codon usage used in the organism. The codon usage can easily be ascertained on the basis of computer analyses of other known genes in the relevant organism.

An expression cassette of the invention is prepared by fusing a suitable promoter to a suitable coding nucleotide sequence and to a terminator or polyadenylation signal. Conventional recombination and cloning techniques are used for this purpose, as are described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes optimal expression of the genes in the host possible. Vectors are well known to the skilled worker and can be found for example in "Cloning Vectors" (Pouwels P. H. et al., editors, Elsevier, Amsterdam-New York-Oxford, 1985).

Host Organisms which can be Used According to the Invention

It is possible with the aid of the vectors or constructs of the invention to prepare recombinant microorganisms which are for example transformed with at least one vector of the invention and can be employed to produce the polypeptides of the invention. The recombinant constructs of the invention described above are advantageously introduced into a suitable host system and expressed. Common cloning and transfection methods familiar to the skilled worker, such as, for example, coprecipitation, protoplast fusion, electroporation, retroviral transfection and the like, are preferably used to bring about expression of said nucleic acids in the particular expression system. Suitable systems are described for example in Current Protocols in Molecular Biology, F. Ausubel et al., editors, Wiley Interscience, New York 1997, or Sambrook et al. Molecular Cloning: A Laboratory Manual. $2^{nd}$ edition, Cold Spring Harbor Laboratory, Cold Spring Harbor Laboratory Press, Cold Spring Harbor, N.Y., 1989.

It is also possible according to the invention to prepare homologously recombined microorganisms. This entails preparation of a vector which comprises at least one segment of a gene of the invention or a coding sequence in which, if desired, at least one amino acid deletion, addition or substitution has been introduced in order to modify, e.g. functionally disrupt, the sequence of the invention (knockout vector). The introduced sequence may, for example, also be a homologue from a related microorganism or be derived from a mammalian, yeast or insect source. The vector used for homologous recombination may alternatively be designed so that the endogenous gene is mutated or otherwise modified during the homologous recombination but still encodes the functional protein (e.g. the regulatory region located upstream may be modified in such a way that this modifies expression of the endogenous protein). The modified segment of the gene of the invention is in the homologous recombination vector. The construction of suitable vectors for homologous recombination is described for example in Thomas, K. R. and Capecchi, M. R. (1987) Cell 51:503.

Suitable recombinant host organisms for the nucleic acid of the invention or the nucleic acid construct are in principle all prokaryotic or eukaryotic organisms. It is advantageous to use as host organisms microorganisms such as bacteria, fungi or yeasts. It is advantageous to use gram-positive or gram-negative bacteria, preferably bacteria of the families Enterobacteriaceae, Pseudomonadaceae, Rhizobiaceae, Streptomycetaceae or Nocardiaceae, particularly preferably bacteria of the genera Escherichia, Pseudomonas, Streptomyces, Nocardia, Burkholderia, Salmonella, Agrobacterium or Rhodococcus. The genus and species Escherichia coli is very particularly preferred. Further advantageous bacteria are additionally to be found in the group of α-proteobacteria, β-proteobacteria or γ-proteobacteria.

The host organism or the host organisms of the invention moreover comprise preferably at least one of the nucleic acid sequences, nucleic acid constructs or vectors which are described in this invention and which code for an enzyme having dehydrogenase activity according to the invention.

The organisms used in the process of the invention are grown or cultured in a manner known to the skilled worker depending on the host organism. Microorganisms are ordinarily grown in a liquid medium which comprises a carbon source, usually in the form of sugars, a nitrogen source, usually in the form of organic nitrogen sources such as yeast extract or salts such as ammonium sulfate, trace elements such as iron, manganese, magnesium salts and, if desired, vitamins, at temperatures between 0° C. and 100° C., preferably between 10° C. to 60° C., while passing in oxygen. The pH of the nutrient liquid can be kept at a fixed value during this, i.e. controlled during the culturing, or not. The culturing can be carried out batchwise, semibatchwise or continuously. Nutrients can be introduced at the start of the fermentation or be subsequently fed in semicontinuously or continuously. The ketone can be added directly for culturing or advantageously after culturing. The enzymes can be isolated from the organisms by the processes described in the examples, or be used for the reaction as crude extract.

Recombinant Preparation of the Polypeptides of the Invention

The invention further relates to processes for the recombinant preparation of polypeptides of the invention or functional, biologically active fragments thereof, where a polypeptide-producing microorganism is cultivated, if desired, expression of the polypeptides is induced, and the latter are isolated from the culture. The polypeptides can also be produced in this way on the industrial scale if this is desired.

The recombinant microorganism can be cultivated and fermented by known processes. Bacteria can be grown for example in TB or LB medium and at a temperature of 20 to 40° C. and a pH of 6 to 9. Suitable cultivation conditions are described for example in detail in T. Maniatis, E. F. Fritsch and J. Sambrook, Molecular Cloning: A Laboratory Manual, Cold Spring Harbor Laboratory, Cold Spring Harbor, N.Y. (1989).

If the polypeptides are not secreted into the culture medium, the cells are then disrupted and the product is obtained from the lysate by known protein isolation methods. The cells may alternatively be disrupted by high-frequency ultrasound, by high pressure such as, for example, in a French pressure cell, by osmolysis, by the action of detergents, lytic enzymes or organic solvents, by homogenizers or by a combination of a plurality of the processes mentioned.

The polypeptides can be purified by known chromatographic methods such as molecular sieve chromatography (gel filtration), such as Q-Sepharose chromatography, ion exchange chromatography and hydrophobic chromatography, and by other usual methods such as ultrafiltration, crystallization, salting out, dialysis and native gel electrophoresis. Suitable methods are described for example in Cooper, F. G., Biochemische Arbeitsmethoden, Verlag Waiter de Gruyter, Berlin, N.Y. or in Scopes, R., Protein Purification, Springer Verlag, New York, Heidelberg, Berlin.

It may be advantageous for isolation of the recombinant protein to use vector systems or oligonucleotides which extend the cDNA by particular nucleotide sequences and thus code for modified polypeptides or fusion proteins which serve, for example, for simpler purification. Suitable modifications of these types are for example so-called tags which act as anchors, such as, for example, the modification known as hexa-histidine anchor, or epitopes which can be recognized as antigens by antibodies (described for example in Harlow, E. and Lane, D., 1988, Antibodies: A Laboratory Manual. Cold Spring Harbor (N.Y.) Press). These anchors can be used to attach the proteins to a solid support, such as, for example, a polymer matrix, which can for example be packed in a chromatography column, or can be used on a microtiter plate or another support.

These anchors can at the same time also be used for recognition of proteins. It is also possible to use for recognition of the proteins conventional markers such as fluorescent dyes, enzyme markers which form a detectable reaction product after reaction with a substrate, or radioactive markers, alone or in combination with the anchors for derivatizing the proteins.

Further Configurations for Carrying Out the Enzymatic Reduction Process of the Invention The dehydrogenases can be used in the process of the invention as free or immobilized enzyme or as catalyst still present in the recombinant producer organism.

The process of the invention is advantageously carried out at a temperature between 0° C. to 95° C., preferably between 10° C. to 85° C., particularly preferably between 15° C. to 75° C.

The pH in the process of the invention is advantageously kept between pH 4 and 12, preferably between pH 4.5 and 9, particularly preferably between pH 5 and 8.

Enantiopure or chiral products mean in the process of the invention enantiomers which exhibit an enantiomer enrichment. Enantiopurities of at least 70% ee, preferably of at least 80% ee, particularly preferably of at least 90% ee, very particularly preferably of at least 98% ee, are preferably achieved in the process.

It is possible to use for the process of the invention growing cells which comprise the nucleic acids, nucleic acid constructs or vectors of the invention. Resting or disrupted cells can also be used. Disrupted cells mean for example cells which have been made permeable by a treatment with, for example, solvents, or cells which have been disintegrated by an enzymic treatment, by a mechanical treatment (e.g. French press or ultrasound) or by another method. The crude extracts obtained in this way are advantageously suitable for the process according to the invention. Purified or partly purified enzymes can also be used for the process. Likewise suitable are immobilized microorganisms or enzymes which can be advantageously used in the reaction.

The process of the invention can be carried out batchwise, semibatchwise or continuously.

The process can advantageously be carried out in bioreactors as described for example in Biotechnology, Volume 3, $2^{nd}$ edition, Rehm et al. editors, (1993), in particular Chapter II.

The following examples are intended to illustrate the invention but without restricting it.

EXPERIMENTAL SECTION

Example 1

Cloning of the Alcohol Dehydrogenase EbN2 from *Azoarcus* sp. EbN1

The sequence of the EbN2 dehydrogenase gene from *Azoarcus* sp. EbN 1 is deposited in databases (SEQ ID NO: 1, [Genbank ID 56475432, Region: 2797788 . . . 2798528]). Oligonucleotides were derived from the nucleic acid sequence of the gene and were used to amplify by known methods the gene from genomic DNA of *Azoarcus* sp. EbN1. The resulting sequence corresponds to the published sequence.

| PCR conditions: | |
| --- | --- |
| 2 µl | of 10*Pfu ultra buffer (Stratagene) |
| 100 ng | of primer #1 |
| 100 ng | of primer #2 |
| 1 µl | of dNTP (10 mM each) |
| ca. 30 ng | of chromosomal DNA from *Azoarcus* sp. EbN1 |
| 1 U | of Pfu ultra DNA polymerase |
| ad 20 µl | $H_2O$ |

Temperature Program:

5 min, 94° C.,
60 sec, 50° C.,
2 min, 72° C.,       } (35 cycles)
60 sec, 94° C.,
10 min, 72° C.,
∞, 10° C.

The PCR product (approx. 751 bp) was digested with the restriction endonucleases NdeI and BamHI and cloned into correspondingly digested pDHE19.2 vector (DE19848129). The ligation mixtures were transformed into *E. coli* XL1 Blue (Stratagene).

The resulting plasmid pDHE-PDH-L was transformed into the strain *E. coli* TG10 pAgro4 pHSG575 (TG10: an RhaA⁻ derivative of *E. coli* TG1(Stratagene); pAgro4: Takeshita, S; Sato, M; Toba, M; Masahashi, W; Hashimoto-Gotoh, T (1987) Gene 61, 63-74; pHSG575: T. Tomoyasu et al (2001), Mol. Microbiol. 40(2), 397-413).

The recombinant *E. coli* are referred to as LU 13151.

Example 2

Cloning of the Alcohol Dehydrogenase ChnA from *Azoarcus* sp. EbN1

The sequence of the dehydrogenase gene ChnA from *Azoarcus* sp. EbN1 is deposited in databases (SEQ ID NO: 3, [Genbank ID 56475432, Region: (complement) 192247 . . . 192993]). Oligonucleotides were derived from the nucleic acid sequence of the gene and were used to amplify by known methods the gene from genomic DNA of *Azoarcus* sp. EbN1. The resulting sequence corresponds to the published sequence.

| PCR conditions: | |
|---|---|
| 2 µl | of 10*Pfu ultra buffer (Stratagene) |
| 100 ng | of primer #3 |
| 100 ng | of primer #4 |
| 1 µl | of dNTP (10 mM each) |
| ca. 30 ng | of chromosomal DNA from *Azoarcus* sp. EbN1 |
| 1 U | of Pfu ultra DNA polymerase |
| ad 20 µl | $H_2O$ |

Temperature Program:

| | |
|---|---|
| 5 min, 94° C., | |
| 60 sec, 50° C., | |
| 2 min, 72° C., | (35 cycles) |
| 60 sec, 94° C., | |
| 10 min, 72° C., | |
| ∞, 10° C. | |

The PCR product (approx. 743 bp) was digested with the restriction endonucleases NdeI and Bg/II and cloned into a pDHE19.2 vector (DE19848129) restricted with NdeI and BamHI. The ligation mixtures were transformed into *E. coli* XL1 Blue (Stratagene).

The resulting plasmid pDHE-PDH-L was transformed into the strain *E. coli* TG10 pAgro4 pHSG575 (TG10: an RhaA⁻ derivative of *E. coli* TG1(Stratagene); pAgro4: Takeshita, S; Sato, M; Toba, M; Masahashi, W; Hashimoto-Gotoh, T (1987) Gene 61, 63-74; pHSG575: T. Tomoyasu et al (2001), Mol. Microbiol. 40(2), 397-413).

The recombinant *E. coli* are referred to as LU 13283.

Example 3

Provision of Recombinant 'Anti-Prelog' Dehydrogenases

LU 13151 or LU 13283 were grown in 20 ml of LB-Amp/Spec/Cm (100 µg/l ampicillin; 100 µg/l spectinomycin; 20 µg/l chloramphenicol), 0.1 mM IPTG, 0.5 g/l rhamnose in 100 ml Erlenmeyer flasks (baffles) at 37° C. for 18 h, centrifuged at 5000*g/10 min, washed once with 10 mM TRIS*HCl, pH 7.0, and resuspended in 2 ml of the same buffer.

Cell-free crude protein extract was prepared by disrupting LU 13151 or LU 13283 cell paste 0.7 ml glass beads (d=0.5 mm) in a vibratory mill (3×5 min with intermediate cooling on ice).

Example 4

Determination of the Activity of the Recombinant 'Anti-Prelog' Dehydrogenases from *Azoarcus* sp. EbN1

6 transformants in each case were grown in 20 ml of LB Amp/Spec/Cm (100 µg/l amp; 100 mg/l spec; 20 µg/lcm) 0.1 mM IPTG 0.5 µl rhamnose in 100 ml Erlenmeyer flasks (baffles) at 37° C. for 18 h, centrifuged at 5000*g/10 min, washed once with 10 mM Tris/HCl pH 7.0, and resuspended in 2 ml of the same buffer.

Cell-free crude extract of the recombinant *E. coli* which comprised the dehydrogenase genes was obtained by cell disruption with 0.7 ml of glass beads (d=0.5 mm) in a vibratory mill (3×5 min with intermediate cooling on ice).

The consumption of reduced cosubstrates can be followed during the reduction of ketones in a photometer at 340 nm. 10 µl of diluted cell-free crude extract (≅10 µg of protein), 10 µmol of ketone and 250 nmol of NADH or NADPH were incubated in 1 ml of 50 mM 1 mM $MgCl_2$, pH 6.5, at 30° C. 1 Unit (1 U) corresponds to the amount of enzyme which reduces 1 µmol of ketone in 1 min.

Example 5

Phenylethanol Analyses

The concentration of acetophenone and phenylethanol can be determined by HPLC. Depending on the choice of the stationary and mobile phases it is possible to determine the ee in addition to the concentration.

| | |
|---|---|
| Stationary phase: | Hydrodex β-6-TBDM (Macherey&Nagel), length: 25 m, Ø: 250 µm, |
| Mobile phase: | helium, split 100:1, total flow rate: 92 ml/min, pressure: 17 psi |
| Flow rate: | 1.0 ml/min |
| Detection: | FID |
| Temperature gradient: | t = 0 min: 90° C., heating at 3°/min to 140° C. |
| Detector temperature: | 250° C. |
| Retention times: | acetophenone: approx. 7.5 min |
| | (1S)-phenylethanol: approx. 12.5 min |
| | (1R)-phenylethanol: approx. 12.1 min |

A calibration series is constructed using authentic material and allows the concentration of unknown samples to be determined.

Example 6

Provision of Glucose Dehydrogenase for Cofactor Regeneration and Cofactor Regeneration with Glucose Dehydrogenase (Enzyme Coupling)

Glucose dehydrogenase can be used for cofactor regeneration. The enzyme can be obtained from commercial (e.g. Jülich Fine Chemicals Order No. 22.10 or 19.10) or own sources. The latter is an *E. coli* XL10 Gold clone which comprises the glucose dehydrogenase gene from *Bacillus subtilis* (Genbank Acc. No. M12276) in the plasmid pUC19 (this construct is called *E. coli* LU11293.

The following medium was made up to ferment E. coli LU11293:

| | |
|---|---|
| 560 g | Yeast extract (65%) |
| 448 g | Tryptone (Difco) |
| 42 g | $KH_2PO_4$ |
| 84 g | $Na_2HPO_4$ |
| 644 g | Glycerol (99%) |
| 100 ml | SL4 solution (5x) |
| 1 g | Tegosipon 3062 |
| | Make up medium to 13.5 l with water, adjust pH to 7.0, remove about 300 ml for preculture, then sterilize at 122° C. for 30 min. Add sterile salt solution* (remove the salt solution for the shaken flasks beforehand; see report). |
| *Salt solution: | 2.1 g of $CaCl_2$* $2H_2O$ |
| | 3.5 g of $MgSO_4$* $7H_2O$ |
| | 14 g of $NH_4Cl$ |
| | 14 ml of ampicillin solution (100 mg/ml) |
| | dissolve in 500 ml of water and sterilize by filtration |

150 ml portions of medium were sterilized in two 1 l Erlenmeyer flasks and completed with 5 ml of sterile salt solution. Inoculation from an LB-ampicillin agar plate was followed by incubation of the precultures at 37° C. and 200 rpm for 12 hours, and addition to the fermentation medium. The fermentation was started at 37° C., 0.1 bar internal pressure, pH 7.0 (controlling with 20% phosphoric acid and 25% NaOH) with an aeration rate of 7.5 l/min and 300 rpm (controlling $pO_2$ at between 20 and 50% with 10-20 l/min inlet air and 500-1500 rpm). After 2 h, 0.1 mM IPTG was added for induction and, after a total of 13 h, the fermentation was terminated. After harvesting and washing of the cells (1.3 kg), they were stored at −20° C. until used (2-20 g/l in the mixture).

Equimolar amounts of glucose and ketone are dissolved with 1-30 U/ml glucose dehydrogenase crude extract and 1-30 U/mL, alcohol dehydrogenase crude extract, 0.02-1 mmol/l NAD or NADP, or NADH or NADPH, in buffer, and incubated at 10-60° C. The pH was kept constant by automatic addition of base.

Example 7

Cofactor Regeneration with Substrate Coupling

Regeneration of the cofactor can also be carried out by the two alcohol dehydrogenases themselves. In this case, addition of a separate regenerating enzyme is unnecessary. The alcohol dehydrogenases ChnA and Ebn2 accept various simple alcohols as reducing agents. They are oxidized to the corresponding carbonyl compounds. Simple alcohols which are suitable for regenerating NADH or NADPH are iso-propanol, butan-2-ol and pentan-2-ol.

Example 8

Cofactor Regeneration with Formate Dehydrogenase (Enzyme Coupling)

Formate dehydrogenase can be used for cofactor regeneration. The enzyme is obtainable from commercial (e.g. Jülich Fine Chemicals Order No. 09.11, 24.11 or 25.10) or from own sources. Regeneration of the cofactors can thus take place also with formate dehydrogenase in analogy to Example 6. In this case, equimolar amounts of formate and ketone are dissolved with 1-30 U/ml formate dehydrogenase crude extract and 1-30 U/ml alcohol dehydrogenase crude extract, 0.02-1 mmol/l NAD or NADP, or NADH or NADPH, in buffer and incubated at 10-60° C. The pH was kept constant by automatic addition of acid.

Example 9

Preparation of R-Phenylethanol with Recombinant Anti-Prelog Dehydrogenases

E. coli LU 13151 or LU 13283 were grown, harvested and disrupted in accordance with Example 3.

Per liter of reaction volume, 0.2 mmol of NAD, 500 U of glucose dehydrogenase, 1 mol of D-glucose, 1 mol of acetophenone, 100-1000 U of alcohol dehydrogenase from LU 13283 or LU 13151 are dissolved in $KP_i$ buffer (50 mM $KP_i$, 1 mM $MgCl_2$, pH 6.5) and incubated at 30° C. The pH was kept constant by automatic addition of 2M NaOH.

It is perfectly plausible that higher final concentrations of R-phenylethanol can be reached if acetophenone is metered in during the course of the reaction (fed-batch procedure). Likewise, reaction in the presence of organic, water-insoluble solvents is possible.

We claim:

1. A process for preparing an optically active alcohol of formula Ia,

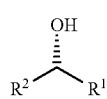

Formula Ia in which $R^1$ and $R^2$ independently are alkyl, alkenyl, aryl, or alkylaryl groups, each of which may be substituted one or more times by alkyl, halogen, SH, $SR^2$, OH, $OR^2$, $NO_2$, CN, CO, $COOR^2$, $NR^2R^3$ or $NR^2R^3R^{4+}X$, where $R^2$, $R^3$ and $R^4$ independently are H or a lower alkyl or lower alkoxy radical, and $X^-$ is a counter ion, with the proviso that $R^1$ is not equal to $R^2$ and $R^1$ is less bulky than $R^2$, by reducing a corresponding ketone with a dehydrogenase having the polypeptide sequence of SEQ ID NO: 2 or having a polypeptide sequence having at least 95% sequence homology to the polypeptide sequence of SEQ ID NO: 2.

2. The process of claim 1, wherein the dehydrogenase is expressed recombinantly in a host organism, and the host organism is incubated in a solution in which the process is carried out.

3. The process of claim 1, wherein the dehydrogenase is expressed recombinantly in a host organism and isolated from said host organism prior to incubating in a solution in which the process is carried out.

4. The process of claim 1, wherein the reduction is carried out at a temperature of 20° C. to 40° C.

5. The process of claim 1, further comprising generating a reduced cofactor by the dehydrogenase, or wherein glucose dehydrogenase, phosphite dehydrogenase, formate dehydrogenase or another alcohol dehydrogenase is used as a cofactor-regenerating system.

6. The process of claim 1, wherein the dehydrogenase is expressed recombinantly in a host organism and a crude extract of said host organism is incubated in a solution in which the process is carried out.

7. The process of claim 6, wherein the crude extract is obtained by disrupting the host organism by high-frequency ultrasound, high pressure, osmolysis, homogenization, by action of detergents, lytic enzymes or organic solvents, or any combination thereof.

* * * * *

SEQUENCE LISTING

<160> NUMBER OF SEQ ID NOS: 8

<210> SEQ ID NO 1
<211> LENGTH: 741
<212> TYPE: DNA
<213> ORGANISM: Azoarcus sp. EbN1
<220> FEATURE:
<221> NAME/KEY: CDS
<222> LOCATION: (1)..(741)
<223> OTHER INFORMATION: EbN2 dehydrogenase

<400> SEQUENCE: 1

```
atg aat cag aaa gtc gca ctc gtc acc ggc gcc atg ggt ggc ctg ggt      48
Met Asn Gln Lys Val Ala Leu Val Thr Gly Ala Met Gly Gly Leu Gly
1               5                   10                  15 acc gct atc tgc cag gcg ctg gca aag gac gga atg aag gtc gtg gcc      96
```

```
                    Thr Ala Ile Cys Gln Ala Leu Ala Lys Asp Gly Met Lys Val Val Ala
                                     20                  25                  30 aat tgt ctc ccc ggc ttt ccg cag aag gat gag tgg ctg gga cgg cag              144
Asn Cys Leu Pro Gly Phe Pro Gln Lys Asp Glu Trp Leu Gly Arg Gln
             35                  40                  45 aag gag ctc ggc ttc gat ttc atc gct gcc gaa ggc gac gta tcg gac              192
Lys Glu Leu Gly Phe Asp Phe Ile Ala Ala Glu Gly Asp Val Ser Asp
 50                  55                  60 tat gac tcc tgt cgc gcg atg gtg gcg aag atc gag ggc gag gtg ggt              240
Tyr Asp Ser Cys Arg Ala Met Val Ala Lys Ile Glu Gly Glu Val Gly
 65                  70                  75                  80 gcg atc gat gtg ctg gtg aac aac gcc ggg atc acc cgc gac aag ttc              288
Ala Ile Asp Val Leu Val Asn Asn Ala Gly Ile Thr Arg Asp Lys Phe
                 85                  90                  95 ttc ccg aag atg gaa aag gtg cag tgg gat gcg gtc atc aac acc aac              336
Phe Pro Lys Met Glu Lys Val Gln Trp Asp Ala Val Ile Asn Thr Asn
             100                 105                 110 ctc aac agc ctt ttc aac gtc act cac cac gtt tcg ccg aag atg gca              384
Leu Asn Ser Leu Phe Asn Val Thr His His Val Ser Pro Lys Met Ala
         115                 120                 125 gaa cgg ggc tat ggc cga atc atc aat att tct tcg gtg aac ggc gtc              432
Glu Arg Gly Tyr Gly Arg Ile Ile Asn Ile Ser Ser Val Asn Gly Val
 130                 135                 140 aag ggc cag gcc ggc cag acc aac tac tcg act gcc aag gcg ggc gtg              480
Lys Gly Gln Ala Gly Gln Thr Asn Tyr Ser Thr Ala Lys Ala Gly Val
145                 150                 155                 160 ctc ggc ttc acg aaa gcc ctt gcc gcg gaa ctg gcg acg aaa ggc gtg              528
Leu Gly Phe Thr Lys Ala Leu Ala Ala Glu Leu Ala Thr Lys Gly Val
                 165                 170                 175 acc gtc aat gcg atc gcg ccg ggc tat atc ggc acc gag atg gtg atg              576
Thr Val Asn Ala Ile Ala Pro Gly Tyr Ile Gly Thr Glu Met Val Met
             180                 185                 190 gcg att cgc gaa gac att cgc cag ggc atc atc gac agc gtc ccg atg              624
Ala Ile Arg Glu Asp Ile Arg Gln Gly Ile Ile Asp Ser Val Pro Met
         195                 200                 205 aag cgc ctg ggc aag ccg gaa gaa atc ggc gct ctg tgc tcc tac ctg              672
Lys Arg Leu Gly Lys Pro Glu Glu Ile Gly Ala Leu Cys Ser Tyr Leu
 210                 215                 220 tct tcc gat ctg gcc ggt tac gtg acc ggc gcg acg atc aac atc aac              720
Ser Ser Asp Leu Ala Gly Tyr Val Thr Gly Ala Thr Ile Asn Ile Asn
225                 230                 235                 240 ggc ggc ctc cac atg tgc tga                                                  741
Gly Gly Leu His Met Cys
                 245

<210> SEQ ID NO 2
<211> LENGTH: 246
<212> TYPE: PRT
<213> ORGANISM: Azoarcus sp. EbN1

<400> SEQUENCE: 2

Met Asn Gln Lys Val Ala Leu Val Thr Gly Ala Met Gly Gly Leu Gly
 1               5                  10                  15

Thr Ala Ile Cys Gln Ala Leu Ala Lys Asp Gly Met Lys Val Val Ala
                 20                  25                  30

Asn Cys Leu Pro Gly Phe Pro Gln Lys Asp Glu Trp Leu Gly Arg Gln
             35                  40                  45

Lys Glu Leu Gly Phe Asp Phe Ile Ala Ala Glu Gly Asp Val Ser Asp
 50                  55                  60

Tyr Asp Ser Cys Arg Ala Met Val Ala Lys Ile Glu Gly Glu Val Gly
```

```
                65                  70                  75                  80
Ala Ile Asp Val Leu Val Asn Asn Ala Gly Ile Thr Arg Asp Lys Phe
                    85                  90                  95

Phe Pro Lys Met Glu Lys Val Gln Trp Asp Ala Val Ile Asn Thr Asn
                100                 105                 110

Leu Asn Ser Leu Phe Asn Val Thr His His Val Ser Pro Lys Met Ala
                115                 120                 125

Glu Arg Gly Tyr Gly Arg Ile Ile Asn Ile Ser Ser Val Asn Gly Val
            130                 135                 140

Lys Gly Gln Ala Gly Gln Thr Asn Tyr Ser Thr Ala Lys Ala Gly Val
145                 150                 155                 160

Leu Gly Phe Thr Lys Ala Leu Ala Ala Glu Leu Ala Thr Lys Gly Val
                165                 170                 175

Thr Val Asn Ala Ile Ala Pro Gly Tyr Ile Gly Thr Glu Met Val Met
                180                 185                 190

Ala Ile Arg Glu Asp Ile Arg Gln Gly Ile Ile Asp Ser Val Pro Met
                195                 200                 205

Lys Arg Leu Gly Lys Pro Glu Glu Ile Gly Ala Leu Cys Ser Tyr Leu
            210                 215                 220

Ser Ser Asp Leu Ala Gly Tyr Val Thr Gly Ala Thr Ile Asn Ile Asn
225                 230                 235                 240

Gly Gly Leu His Met Cys
                245

<210> SEQ ID NO 3
<211> LENGTH: 747
<212> TYPE: DNA
<213> ORGANISM: Azoarcus sp. EbN1
<220> FEATURE:
<221> NAME/KEY: CDS
<222> LOCATION: (1)..(747)
<223> OTHER INFORMATION: dehydrogenase

<400> SEQUENCE: 3 atg ctg ctc gaa ggg aaa acc gcg ctg gtg acg ggt gcc ggc aac ggc      48
Met Leu Leu Glu Gly Lys Thr Ala Leu Val Thr Gly Ala Gly Asn Gly
1               5                   10                  15 atc ggc cgc acc atc gcg ctc acc tac gcc gcc gaa ggg gcg aac gtc      96
Ile Gly Arg Thr Ile Ala Leu Thr Tyr Ala Ala Glu Gly Ala Asn Val
                20                  25                  30 gtt gtt tcc gac atc agt gac gaa tgg ggc cgg gaa aca ctc gcc ctg     144
Val Val Ser Asp Ile Ser Asp Glu Trp Gly Arg Glu Thr Leu Ala Leu
            35                  40                  45 atc gaa ggc aag ggc gga aaa gcc gtt ttc caa cac gcc gac acc gcc     192
Ile Glu Gly Lys Gly Gly Lys Ala Val Phe Gln His Ala Asp Thr Ala
50                  55                  60 cac ccc gaa gac cat gac gag ctg atc gcc gcg gcc aaa cgc gcc ttc     240
His Pro Glu Asp His Asp Glu Leu Ile Ala Ala Ala Lys Arg Ala Phe
65                  70                  75                  80 ggc cgc ctc gac att gcc tgc aac aac gcc ggc atc agc ggc gaa ttc     288
Gly Arg Leu Asp Ile Ala Cys Asn Asn Ala Gly Ile Ser Gly Glu Phe
                85                  90                  95 acc cct acc gcg gaa acg acc gac gcc cag tgg caa cga gtc atc ggc     336
Thr Pro Thr Ala Glu Thr Thr Asp Ala Gln Trp Gln Arg Val Ile Gly
                100                 105                 110 atc aac ctg tcg ggc gtg ttc tac ggc gtg cgt gcg cag att cgc gcc     384
Ile Asn Leu Ser Gly Val Phe Tyr Gly Val Arg Ala Gln Ile Arg Ala
            115                 120                 125 atg ctc gaa acc gga ggc ggc gcg atc gtc aat att tct tcc att gcc     432
```

```
Met Leu Glu Thr Gly Gly Gly Ala Ile Val Asn Ile Ser Ser Ile Ala
    130                 135                 140 ggg cag atc ggc atc gag ggc atc acg ccc tac acc gcc gcc aag cac     480
Gly Gln Ile Gly Ile Glu Gly Ile Thr Pro Tyr Thr Ala Ala Lys His
145                 150                 155                 160 ggc gtg gtg ggt ctg acg aaa acg gtc gcc tgg gaa tat ggc agc aag     528
Gly Val Val Gly Leu Thr Lys Thr Val Ala Trp Glu Tyr Gly Ser Lys
                165                 170                 175 ggc atc cgc atc aat tcg gtc ggt ccg gcc ttc atc aat acc acg ctg     576
Gly Ile Arg Ile Asn Ser Val Gly Pro Ala Phe Ile Asn Thr Thr Leu
                180                 185                 190 gtt cag aac gtt ccc ctc gaa aca cgc cgg cag ctc gaa cag atg cac     624
Val Gln Asn Val Pro Leu Glu Thr Arg Arg Gln Leu Glu Gln Met His
        195                 200                 205 gcc ctg cgc cgc cta ggc gaa acg gaa gaa gtc gcc aat ctc gtc gcc     672
Ala Leu Arg Arg Leu Gly Glu Thr Glu Glu Val Ala Asn Leu Val Ala
210                 215                 220 tgg ctg agc agc gac aag gcc agc ttc gtc acc ggc agc tat tac gcg     720
Trp Leu Ser Ser Asp Lys Ala Ser Phe Val Thr Gly Ser Tyr Tyr Ala
225                 230                 235                 240 gtc gac ggc ggc tac ctc gca cga tga                                 747
Val Asp Gly Gly Tyr Leu Ala Arg
                245

<210> SEQ ID NO 4
<211> LENGTH: 248
<212> TYPE: PRT
<213> ORGANISM: Azoarcus sp. EbN1

<400> SEQUENCE: 4

Met Leu Leu Glu Gly Lys Thr Ala Leu Val Thr Gly Ala Gly Asn Gly
1               5                   10                  15

Ile Gly Arg Thr Ile Ala Leu Thr Tyr Ala Ala Glu Gly Ala Asn Val
                20                  25                  30

Val Val Ser Asp Ile Ser Asp Glu Trp Gly Arg Glu Thr Leu Ala Leu
            35                  40                  45

Ile Glu Gly Lys Gly Gly Lys Ala Val Phe Gln His Ala Asp Thr Ala
    50                  55                  60

His Pro Glu Asp His Asp Glu Leu Ile Ala Ala Lys Arg Ala Phe
65                  70                  75                  80

Gly Arg Leu Asp Ile Ala Cys Asn Asn Ala Gly Ile Ser Gly Glu Phe
                85                  90                  95

Thr Pro Thr Ala Glu Thr Thr Asp Ala Gln Trp Gln Arg Val Ile Gly
                100                 105                 110

Ile Asn Leu Ser Gly Val Phe Tyr Gly Val Arg Ala Gln Ile Arg Ala
            115                 120                 125

Met Leu Glu Thr Gly Gly Gly Ala Ile Val Asn Ile Ser Ser Ile Ala
    130                 135                 140

Gly Gln Ile Gly Ile Glu Gly Ile Thr Pro Tyr Thr Ala Ala Lys His
145                 150                 155                 160

Gly Val Val Gly Leu Thr Lys Thr Val Ala Trp Glu Tyr Gly Ser Lys
                165                 170                 175

Gly Ile Arg Ile Asn Ser Val Gly Pro Ala Phe Ile Asn Thr Thr Leu
                180                 185                 190

Val Gln Asn Val Pro Leu Glu Thr Arg Arg Gln Leu Glu Gln Met His
        195                 200                 205

Ala Leu Arg Arg Leu Gly Glu Thr Glu Glu Val Ala Asn Leu Val Ala
    210                 215                 220
```

Trp Leu Ser Ser Asp Lys Ala Ser Phe Val Thr Gly Ser Tyr Tyr Ala
225                 230                 235                 240

Val Asp Gly Gly Tyr Leu Ala Arg
                245

```
<210> SEQ ID NO 5
<211> LENGTH: 30
<212> TYPE: DNA
<213> ORGANISM: Artificial Sequence
<220> FEATURE:
<223> OTHER INFORMATION: PCR-Primer

<400> SEQUENCE: 5
gcgattgcat atgaatcaga aagtcgcact                                    30

<210> SEQ ID NO 6
<211> LENGTH: 32
<212> TYPE: DNA
<213> ORGANISM: Artificial Sequence
<220> FEATURE:
<223> OTHER INFORMATION: PCR-Primer

<400> SEQUENCE: 6
gcgcaggctt cggatcctgc atcagcacat gt                                 32

<210> SEQ ID NO 7
<211> LENGTH: 30
<212> TYPE: DNA
<213> ORGANISM: Artificial Sequence
<220> FEATURE:
<223> OTHER INFORMATION: PCR-Primer

<400> SEQUENCE: 7
gcgattgcat atgctgctcg aagggaaaac                                    30

<210> SEQ ID NO 8
<211> LENGTH: 30
<212> TYPE: DNA
<213> ORGANISM: Artificial Sequence
<220> FEATURE:
<223> OTHER INFORMATION: PCR-Primer

<400> SEQUENCE: 8
ctgatagatc ttagtgagcg atgaggatca                                    30
```